(12) United States Patent
Koehler

(10) Patent No.: US 7,118,711 B1
(45) Date of Patent: Oct. 10, 2006

(54) MICROCOLUMN REACTOR

(75) Inventor: Johann Michael Koehler, Golmsdorf (DE)

(73) Assignee: Clondiag Chip Technologies GmbH, Jena (DE)

( * ) Notice: Subject to any disclaimer, the term of this patent is extended or adjusted under 35 U.S.C. 154(b) by 0 days.

(21) Appl. No.: 09/914,874

(22) PCT Filed: Feb. 25, 2000

(86) PCT No.: PCT/EP00/01701

§ 371 (c)(1),
(2), (4) Date: Sep. 5, 2001

(87) PCT Pub. No.: WO00/53308

PCT Pub. Date: Sep. 14, 2000

(30) Foreign Application Priority Data

Mar. 5, 1999 (DE) .................................. 199 10 392

(51) Int. Cl.
*B01L 11/00* (2006.01)

(52) U.S. Cl. .................. 422/101; 422/99; 422/100; 436/180; 436/164; 436/165; 204/601; 204/603

(58) Field of Classification Search ................ 422/101, 422/178, 99–100; 436/164–165; 204/601, 204/603

See application file for complete search history.

(56) References Cited

U.S. PATENT DOCUMENTS 5,120,511 A * 6/1992 Luft ........................... 422/86

(Continued)

FOREIGN PATENT DOCUMENTS

| WO | WO 93 22053 | 11/1993 |
| WO | WO 96 03212 | 2/1996 |
| WO | 98/00231 | 1/1998 |

OTHER PUBLICATIONS

Jun Gao, Jingdong Xu, Laurie E. Locascio, and Cheng S. Lee, Analytical Chemistry Jun. 1, 2001, vol. 73, No 11 2648-2655.*

(Continued)

*Primary Examiner*—Jill Warden
*Assistant Examiner*—Jyoti Nagpaul
(74) *Attorney, Agent, or Firm*—Jordan and Hamburg LLP (57) ABSTRACT

The invention relates to a microcolumn reactor for carrying out reactions on solid phases and/or with biological cells. The aim of the invention is to provide a microcolumn reactor for processes of synthesis and separation on small sample volumina that replaces an alternating sequence of binding and elution processes on a phase that is stationary bound during a test series and makes it possible to exchange the stationary phase, for example once it has been loaded. To this end, the microcolumn reactor consists of at least one first and one second substrate wafer (1; 2) that are linked with one another across their surfaces. At least one of the substrate wafers (1; 2) is provided with an elongate channel (3) which comprises in a defined section (a) of its length two passage openings (41, 42) that are implemented in the opposite substrate wafer. Said openings (41, 42) are separated from the channel (3) by a partially permeable sieve-type membrane (5). The areas of acceptance (51) of said membrane have a diameter that is chosen in such a manner as to specifically prevent microbeads and/or cells introduced into the channel from entering the passage openings (41, 42). The channel (3) is provided with at least two further openings (61, 62) outside the section (a) that is comprised by the passage openings (41, 42). Said further openings permit the microbeads and/or cells that are provided above the section (a) to be introduced and/or displaced by applying a fluid pressure (p). Means are provided that temporarily close at least one of the passage openings (41, 42) and one of openings (61, 62).

15 Claims, 6 Drawing Sheets

U.S. PATENT DOCUMENTS

| | | | |
|---|---|---|---|
| 5,304,487 A | | 4/1994 | Wilding et al. |
| 5,441,597 A | * | 8/1995 | Bonne et al. .................. 216/2 |
| 5,534,328 A | | 7/1996 | Ashmead et al. |
| 5,585,011 A | * | 12/1996 | Saaski et al. .................. 216/2 |
| 5,690,763 A | | 11/1997 | Ashmead et al. |
| 5,962,081 A | * | 10/1999 | Ohman et al. .............. 427/534 |
| 6,117,396 A | * | 9/2000 | Demers ...................... 422/100 |
| 2002/0058332 A1 | * | 5/2002 | Quake et al. ............ 435/288.3 |

OTHER PUBLICATIONS

Kessler, H.G., Lenbensmittel- und Bioverfahrenstechnik — Verlag A. Kessler, Freising 1988 pp. 446-450.

Ullmanns Enzyklopaedie der technischen Chemie, VCH Verlags GmbH, Weinheim, 1973, pp. 434-436 and p. 449.

* cited by examiner

MICROCOLUMN REACTOR

BACKGROUND OF TE INVENTION

The invention relates to a microcolumn reactor for carrying out reactions on solid phases and/or with biological cells. Thereby, the proposed microcolumn reactor can be applied, for example, with advantage in the following synthesis processes and separation processes:
- in Grignard reactions and in the manufacture of other metal-organic compounds,
- in drying of solvents by aid of metallic or oxidic dessicants,
- in ion exchange processing, and
- in the extraction of solid phases.

More particularly, the invention will find application in the field of complex combinatorial-chemical operations or in screening operations or in automatically carrying out biological screening processing.

Sample particles ("beads" or "Perlen") have been used in separations and synthesis in the laboratory work for decades. These particles mostly are glass or polymeric globules that have diameters of 0.01 mm up to 1 mm, typically about 0.1 mm, which are filled, dry or pre-swelled, as a loose material into a receptacle where they are then flushed by a liquid, whereby an adsorption process or a reaction process takes place between the solid phase surface of the particles and the liquid surrounding the particles. Methods of the column chromatography (for example, gel filtration), of the column extraction, of the immundiagnosis, of the bio-molecule purification (for example, DNA cleaning), as well as of the homogeneous and heterogeneous synthesis (for example, of oligonucleotides, peptides or combinatorial substance libraries) utilize these techniques. With all these methods and devices, a solid-phase is stationarily integrated during the reaction in the reaction vessel, whereby reactants are bound to the solid phase or the latter serves as a reaction surface. The processes comprise a sequence of individual binding operations and separation operations. In such devices, a removal of the stationarily arranged solid phase from the reactor in the course of an operation series is either not provided for, or not possible or it is time consuming and not very practical.

SUMMARY OF THE INVENTION

It is an object of the present invention to provide a microcolumn reactor for synthesis and separation processes on small sample volumes, by aid of said microcolumn reactor, instead of an alternating sequence of binding and elution processes of a solid phase that is stationarily bound during an operation series, an exchange of the stationary solid phase, for example, after loading can be performed in order to more efficiently separate, for example, complex substance mixtures or particles and cells and to carry out combinatorial syntheses more easily and faster.

The object is realized by the features of the invention. Advantageous embodiments are also described.

The very essence of the invention consists in that a microcolumn reactor for carrying out reactions on solid phases and/or biological cells is provided, which is comprised of at least a first and a second substrate wafer which are hiked with one another in a common plane and whereby at least one longitudinally extending channel is provided in at least one of the substrate wafers, said channel, in a preselectable section of its longitudinal extension, is captured by two passage openings which are provided in and into the opposite substrate wafer. The passage openings are separated from the channel by a partially permeable sieve-like membrane, the transmission range of which is so dimensioned as to preselectably prevent the microbeads and/or cells, which are introduced into the channel, from entering the passage openings. The channel is provided with at least two further openings which are disposed outside the section defined by the passage openings, said further openings are adapted to introduce and/or to displace the microbeads and/or the cells provided in, respectively above the section by applying a fluid pressure. At least one of the passage openings and one of the further openings are adapted to be closed.

DETAILED DESCRIPTION OF THE INVENTION

The invention will be explained in more detail by virtue of schematical embodiments. There is shown in.

Figure 1:
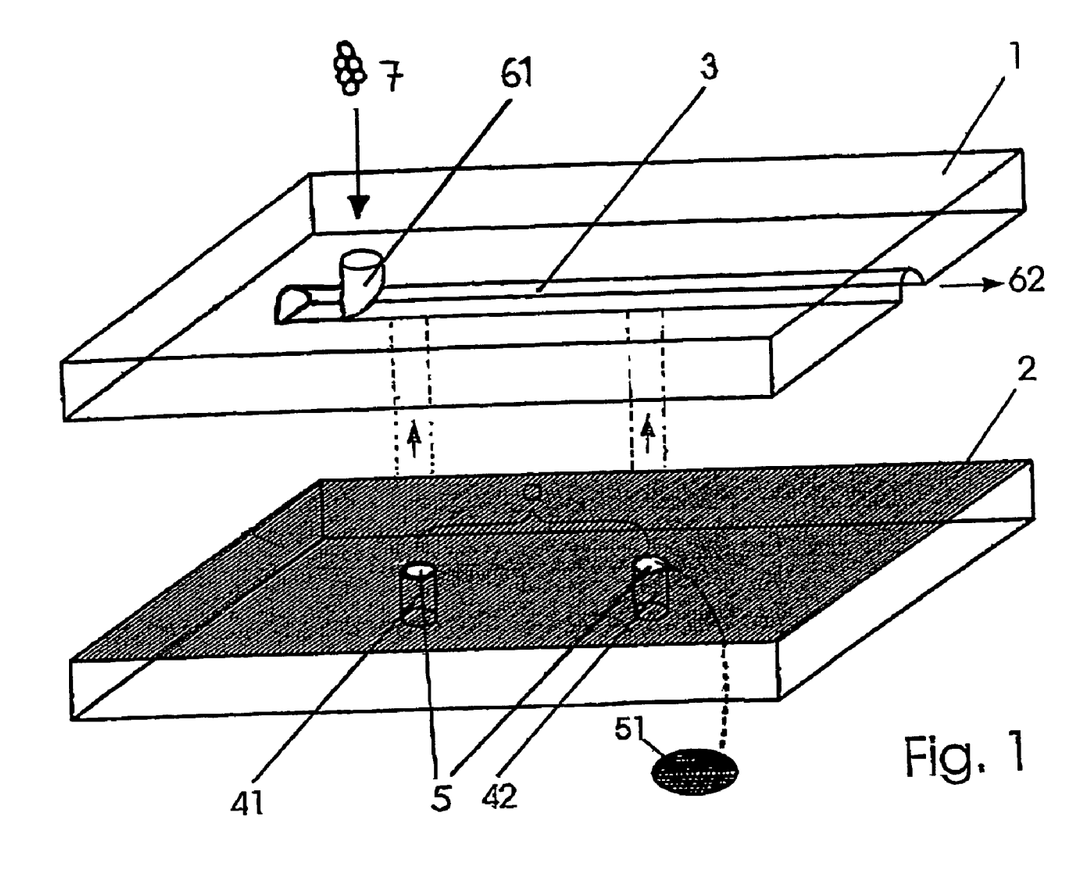
FIG. 1 an exploded view of a first embodiment of a microcolumn reactor with its functionally essential components, FIG. 2 an exploded view of a second embodiment of a microcolumn reactor with its functionally essential components, FIG. 2a another type of connection of the passage openings with inlet channels and outlet channels, respectively, FIG. 3 a longitudinal section through a part of the embodiment according to FIG. 1 or FIG. 2, FIGS. 4 and 5 possible arrangement designs of a plurality of microcolumn reactors, FIG. 6 a block diagram exemplifying the connection of a plurality of microcolumn reactors for the synthesis of a special substance library, and FIGS. 7a–d a further embodiment of a microcolumn reactor in different steps of manufacture.

In FIG. 1, number 1 designates of a first embodiment of a microcolumn reactor shown in an exploded view with its functionally essential components. According to FIG. 1, the microcolumn reactor is comprised of two substrate wafers 1, 2, having, in the present example, an elongated channel 3 inserted into said first substrate wafer 1 which here is made of glass and has the dimensions of 15 mm·8 mm·1 mm. The channel 3 is given a width of 1 mm, a depth of 100 μm and a length of 10 mm. Said channel is connected via two openings 61, 62, which here are bore holes, to two fluid connection ports (not shown). As to the second substrate wafer 2, a silicon chip having the dimensions of 15 mm·8 mm·0.5 mm has been selected, into which two passage openings 41, 42 have been worked in in such a manner that, when precisely position fitted relative to the glass plate 1, they capture a section a, which in the example comes to lie across the end portions of the channel 3. The passage openings 41, 42 are covered by a partially permeable membrane of the sieve type, here in the form of a porous membrane of siliconoxinitride. In the example, the membrane has a thickness of 2 μm and the transmission areas 51 of the membrane have pores with diameters of 5 μm. Depending on the special case of application and on the microbeads 6 to be used, the actual sizes of the transmission area 51 can be variably and preselectably designed. The pore membrane has the task to hold back the particles or cells 7 that are to be introduced into the channel 3. Furthermore and depending on the kind of application of the microcolumn reactor, the membrane 5 can, within the frame of the invention, be formed by a nano-porous thin layer membrane, the pore size of which can be selected to lie within a range between 5 . . . 500 nm.

Figure 3:
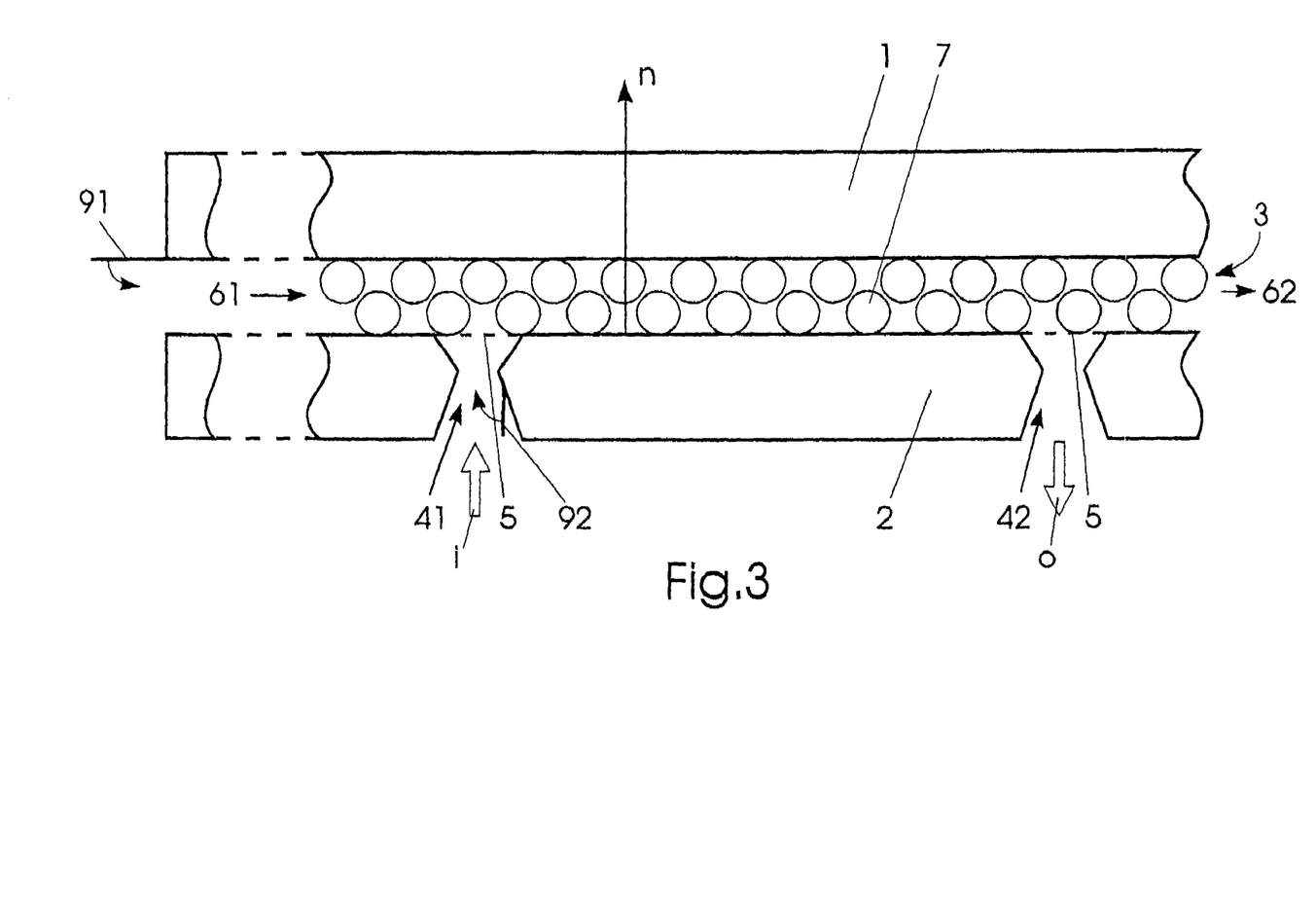

If there is intended to provide to the passage openings 41, 42 a shape as indicated in FIG. 3, where the passage openings, being in parallel to the surface normal n of the second substrate wafer 2, are formed by two channel ranges in the shape of two truncated pyramids standing via their small base faces top-to-top, then a Si(100)-wafer is used for the substrate wafer 2 which on both of its faces is provided with a suitable etching mask (for example, Si-oxinitride). Said mask, on the front side, forms an array of microwindows, the dimensions of which define the pore width. Typically, a pore width of 5 μm is realized. This can easily be manufactured by conventional means of the photolithography and the etching technique. Two windows are structurized from the rear side of the Si-wafer centrally to this pore structure in such a way that two channel ranges in the shape of two truncated pyramids result from the etching procedure carried out on both sides, whereby the surfaces of said channels which are in opposition to the first substrate wafer 1 are closed by sieve bottoms.

Figure 7A:
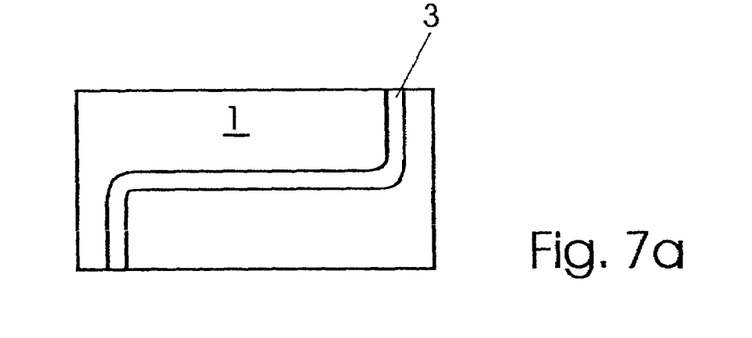
Figure 7B:
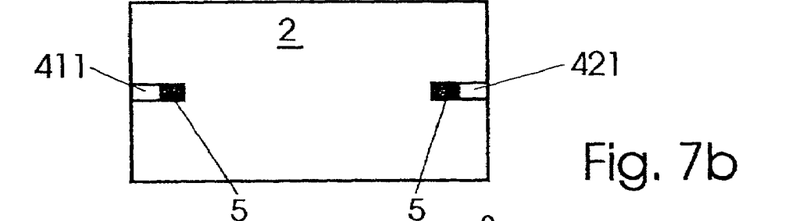
Figure 7C:
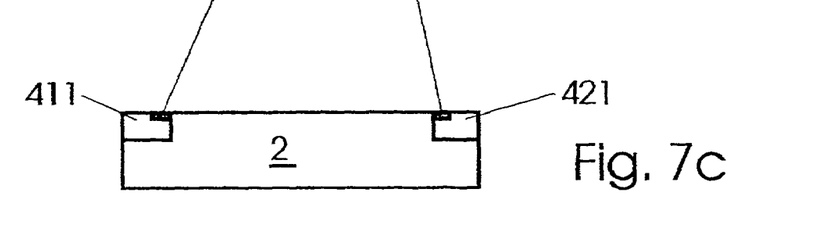
Figure 7D:
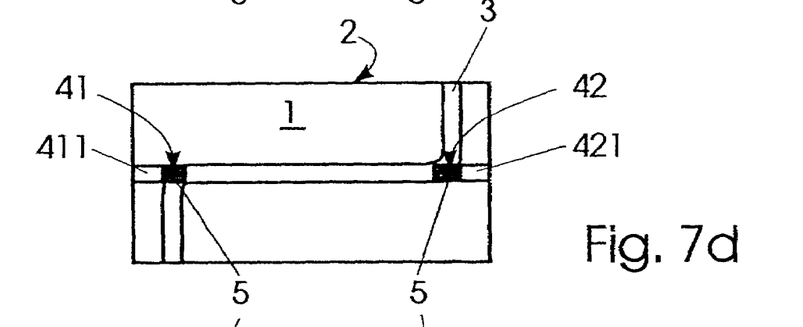

When at the same time with generating the passage openings 41, 42 channel structures adapted for a fluid contact of the mobile phase within the substrate plane of the substrate wafer 2 have to be generated, so that the connection ports 41, 42 are, for example, laterally funneled out from the leading faces of the microcolumn reactor, then in the present example, there is a Si-wafer (in a 100-orientation for inclined channel walls or in a 110-orientation for vertical channel walls) employed for the substrate wafer, which is provided with a sieve pore membrane mask structure 5 which, in the range of the extending channel 411, 412, is accompanied by a window which corresponds to the channel width and which extends up to the rim of the chip (refer to FIGS. 7a–d). The rear side of the Si-wafer is entirely covered by a protective coat (for example $Si_3N_4$) which is resistant to etching. At first, the Si-wafer is etched in an etching bath which acts isotropically (for example, on F-basis) in such a way that the stems between the individual pores of the sieve structure mask are completely underetched. Subsequently the etching is continued in an anisotropic etching bath (for example, on a KOH-basis), to obtain the inclined and vertical, respectively, edges of the channel. In FIGS. 7a–d the results of the foregoing procedure is shown by means of an exemplary structure. Thereby in FIG. 7a a channel 3 can be seen which is inserted into the first substrate wafer 1. FIG. 7b shows the structure inserted into the first substrate wafer 1, including the formed channel sections 411 and 421 extending up to the rim portion of the substrate, whereby FIG. 7c shows the relations represented in FIG. 7b in a lateral section, and FIG. 7d illustrates in a transparent plan view the orientation of the individual parts mentioned relative to one another with the first substrate wafer and the second substrate wafer being connected to one another.

The first and the second substrate wafers 1,2 described in connection with FIG. 1 are connected with one another by anodic bonding after manufacture of the structures described.

Figures 2, 2A:
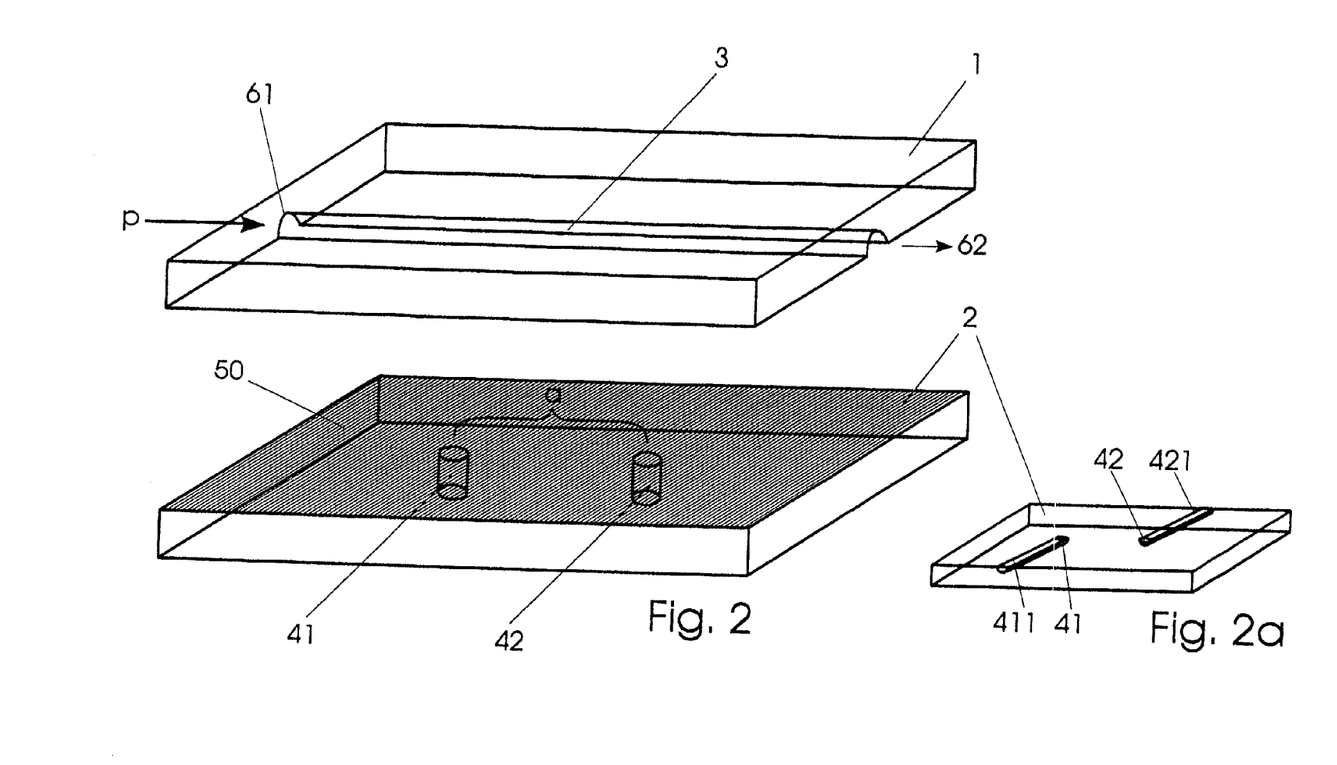

The special embodiments described hereinbefore are particularly advantageously to be manufactured by conventional working steps of approved microstructuring techniques, however, the invention is not limited thereto. It is possible as well, to use a glass-wafer and/or a wafer made of a synthetic material for the first and/or the second substrate wafers 1,2, whereby the channel 3 is inserted into the first substrate wafer 1 and the surface of the second substrate wafer 2 opposing said first substrate wafer 1 is entirely covered by a membrane in which at least in the range of the passage openings 41, 42 a microstructurized perforation is provided in order to form the transmission areas 51. In particular, here the second substrate wafer 2 can be provided with a perforated polymeric foil 50 covering the substrate wafer, as schematically indicated in FIG. 2. Such an embodiment even allows for other pathways for the channel, as indicated in FIG. 2a by way of example with respect to the channel pathways 411 and 421 in the substrate wafer 2.

In FIG. 3 there is shown a longitudinal section through a part of the embodiments according to FIGS. 1 and 2 which have already been described. Thereby it is rendered visible how the channel 3 with the substrate wafers 1, 2 in their assembled state is filled with the solid phase, here in the form of microbeads 7. With the present proposal it is not necessary to have extreme packing densities of the stationary phase 7. It is only important that the distances between the particles of the stationary phase 7 are so dimensioned that a molecule contacts the stationary phase frequently enough during its dwell time in the reactor chamber, which is here to be understood as the section of the channel 3 between the passage openings 41, 42. This will already be given with particle sizes in the mean to the lower micrometer range at hold-up times of less than one second, partially in the lower millisecond range. The definition of the particle sizes and/or of the cells to be retained or passed through depends on the given actual task and on the pore sizes, which have to be adapted accordingly, of the partially permeable sieve-like membrane 5. The pore size has to be so dimensioned that any blocking of the pores is eliminated. In FIG. 3 there is also schematically indicated that the individual flow paths in the microcolumn reactor shown are selectively closeable by at least two valves 91, 92. The openings 42, 62 can each optionally be closed by a respective further valve, not shown in FIG. 3. This permits a freely selective addressing of the two inlets 61, 41 and of the two outlets 42, 62 of the microcolumn reactor. Thus a microcolumn reactor is provided in which not only the mobile phase, for example, a homogeneous fluid, the flow path of which is indicated in FIG. 3 by the arrows i and o, can be moved but also the stationary phase, here the microbeads 7. The closing of one respective inlet flow or outlet flow now permits to selectively transport the mobile phase and/or the stationary phase 7 as a suspension. Thus a fast exchange of separation material will be possible, and there can be even built up solid phase separation logics and synthesis logics by a combination of a plurality of the microcolumn reactors described. Due to the micro-fluidic separation of the mobile phase and the stationary phase, specifical binding processes and separation processes can thus be carried out, which will be described in more detail in the following.

Figure 4:
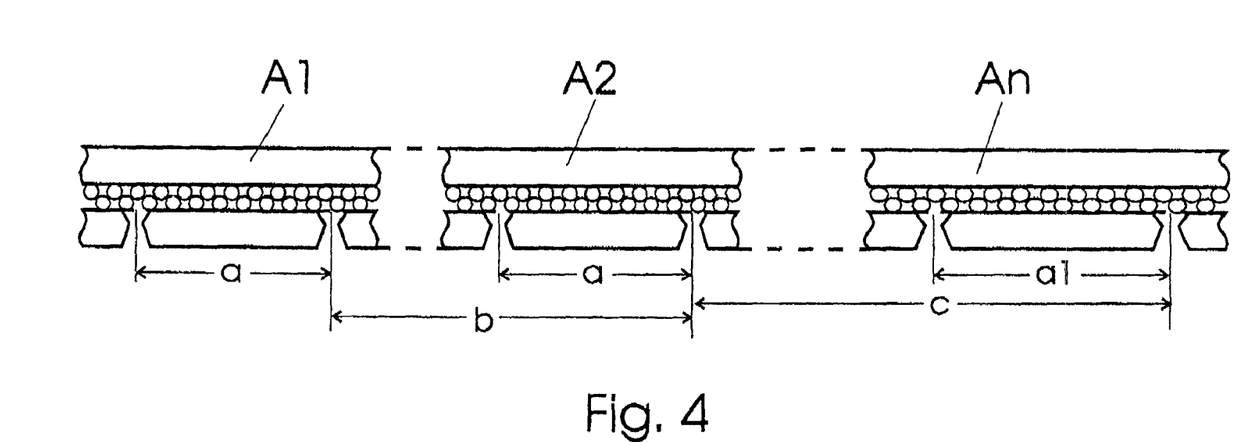
Figure 5:
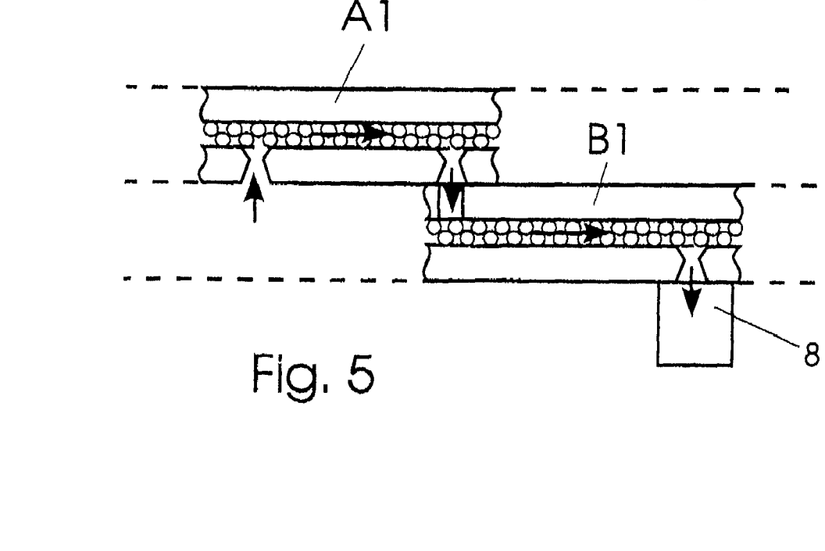

In FIGS. 4 and 5 there are schematically indicated several possible forms of arrangement of a plurality of microcolumn reactors. Thereby, depending on the kind of realization, the microcolumn reactors can be, in analogy to FIGS. 1 and 2, of a discrete design and can be combined with one another. Alternatively, as shown in FIGS. 4 and 5, a plurality of such microcolumn reactors can be in a linear combination (FIG. 4) of a first and a second substrate wafer each, or there can be connections between a plurality of such microcolumn reactors in different planes (FIG. 5), whereby one respective plane is designed in analogy to FIG. 4. Depending on the preselectable reaction procedure, the proper reactor sections, defined by the length of section a, whereby the passage openings 41, 42 determine the channel 3 length, can be arranged to one another equidistantly by a distance b or in a variably selectable distance c. It is also possible to select different lengths for the distances of the passage openings 41, 42 from one reactor to the next, refer to distance a and a1 in FIG. 4. The mentioned feasibilities are only determined by the reactions to be carried out with the microcolumn reactors. Further components, in particular such also designed in microsystem techniques, as for example, optical detectors, analysis units, calorimeters, electrochemical detectors etc., can be comprised in an interconnection of a plurality of microcolumn reactors, as indicated, only schematically, by such a unit 8 in FIG. 5.

The proposed microcolumn reactor and its multifold application by an interconnection of a plurality of individual microcolumn reactors is particularly suited for performing automated processes of agent development by means of bead-bound solid phase synthesis. A plurality of such microcolumn reactors can be connected to one another and by way of valves, which have to be provided, in order to obtain fluid-logics that permit to carry out, for example, more complex combinatorial-chemical or screening operations in a micro-automated way. Particularly in biologic screening processes, also cells can be introduced into the system instead of the micro-beads, indicated in FIG. 3. The reactor is also suited for the micro-modular combination with micro-flow cuvettes in micro-photometric, micro-fluorimetric, or micro-chemo-luminometric measurements.

The proposed microcolumn reactor permits a re-charging by pushing new reactants (micro-beads and/or cells) through the channel 3 in that a fluid pressure p is applied so that a further variability is given for the entire device at a simultaneously lowest possible dead volume.

The represented advantageous possibilities of application will be indicated in more detail by way of the following examples.

At first, the synthesis of a library of 4 tripeptide gly-val-leu, gly-gly-leu, gly-val-ala, and gly-gly-ala will be described in a micro-reactor fluid system.

Figure 6:
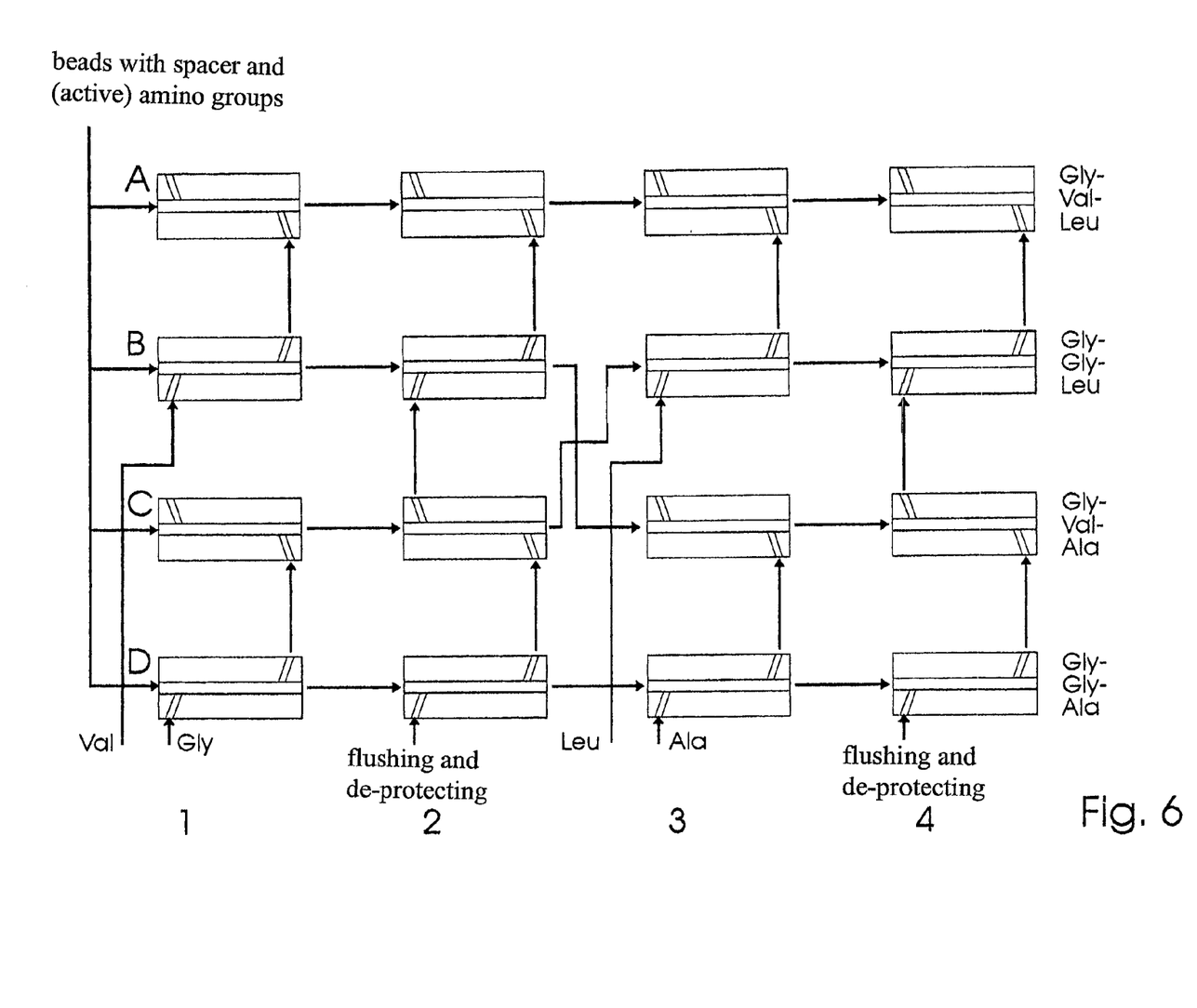

In the example, a system of 16 microcolumn reactors will be employed, which are fluidically interconnected, as indicated in FIG. 6. At first, the micro-reactors A1 and B1 as well as C1 and D1 are charged with micro-beads in the form of polystyrene-synthesis-beads, to the surfaces of which the amino acid glycine is coupled by an ester linkage to a benzyl group as a spacer. After blocking the fluid channels for the stationary phases (beads) via the channels, the inlets and outlets of which are provided with sieve bottoms, the four microcolumn reactors are flushed for the mobile phases in pairs (A/B) by a 1:1 mixture of a warm solution of dicyclohexylcarbodiimide and vale, respectively (C/D) by a 1:1 mixture of warm solution of dicyclohexylcarbodiimide and glycine. Thereby the amino groups of the added amino acids are protected by tertiary-butyloxycarbonyl-groups. After the first flushing step, all the stationary phases are moved on to the module row 2 by a respectively applied fluidic pressure, and are flushed there by the series-connected channels to be ready for the mobile phase and are de-protected by passing through a slightly aqueous trifluoroacetic acid. Subsequently, the fluid phases are moved an to the module group 3, whereby the stationary phase of B2 is moved on to C3 and that of C2 on to B3. In the module row 3, there is carried out, in analogy to the module row 1, the transfer by protected amino acids, whereby leucine is now added instead of valine, and alanine is now added instead of glycine. After this operation and after a first elution step, the stationary phases are moved on to the module row 4 and there the protective groups are separated. Subsequently the four groups of synthesis-beads are then removed at separate outlets and, in order to release the tripeptides, the benzylester links are separated.

In a further example for application the manufacture of ethyl-grignard from ethylchloride for micro-fluid-syntheses will be described.

At first, as a stationary phase, a suspension of magnesium powder in dry ethylether is loaded into a microcolumn reactor. After closing the channel for this stationary phase, and to make ready for the mobile phase, ether is displaced by a warm solution of ethylchloride in ether via the inlet and the outlet. At the outlet of the mobile phase ethyl-grignard is taken out as an ether solution.

The microcolumn reactor can be utilized in the manner of a chip-cartridge also for rendering available almost any grignards and other metal-organic compounds for micro-fluid-syntheses in the form of a chip. The system is particularly advantageous since the solutions can easily be kept anhydrous and oxygen-free (for example, in contrast to microtiter plates and nanotiter plates) and, due to the small reaction volume, the emitted heat of reaction can easily be dissipated. Thus an otherwise dangerous overheating of the reactor cannot occur.

According to the various possible applications described in the initial part of the specification, the proposed microcolumn reactor can be utilized with advantage in many a way.

All features disclosed in the specification, in the subsequent claims, and in the drawing can be substantial for the invention both, individually and in any combination with one another.

LIST OF REFERENCE NUMERALS

1—first substrate wafer
2—second substrate wafer
3—channel
41, 42—passage openings
411, 421—channel sections (in the second substrate wafer)
5—partially permeable sieve-like membrane
50—polymeric foil
51—transmission area (pores)
61, 62—openings (in the first substrate wafer)
7—micro-beads and/or cells
8—components such as, for example, optical detectors, analysis units, calorimeters, electrochemical detectors etc.
91, 92—valves
a, a1—section between passage openings
b—equidistant spaces between associated passage openings
c—different distances between associated passage openings
i—inlet for the mobile phase
o—outlet for the mobile phase
n—surface normal
p—fluidic pressure
A1 to D4—microcolumn reactors

The invention claimed is:

1. Microcolumn reactor for carrying out reactions on solid phases and/or biological cells comprising at least a first and a second substrate wafer being engaged to one another in a common plane, whereby at least one longitudinally extending channel is inserted into at least one of said substrate wafers, said channel, in a preselectable section of its length, being captured by two passage openings, which are passed through the an opposite substrate wafer, wherein the passage openings are separated from the channel by a partially permeable sieve-like membrane, the membrane having transmission areas so dimensioned that they preselectably prevent micro-beads and/or cells, which are introduced into the channel, from entering into the passage openings, and the channel is provided with at least two further openings outside of the section captured by said passage openings, said at least two further openings being adapted to enable a loading and/or a displacement of the micro-beads and/or cells, provided above the section captured by said preselectable channel section, by applying a fluidic pressure, and further comprising means for temporarily closing at least one of the passage openings and one of the further openings.

2. The microcolumn reactor as claimed in claim 1, wherein glass is selected for the first substrate wafer and a silicon wafer for the second substrate wafer, whereby the channel is inserted into the glass plate and the surface of the silicon wafer opposing said glass plate is entirely covered by a coat, into which a micro-structurized perforation is provided at least in the section of the passage openings, said micro-structurized perforation being for forming transmission areas.

3. The microcolumn reactor as claimed in claim 1, wherein at least one of a glass plate and a plate made of synthetic material is selected for the first and/or for the second substrate wafer, the channel is inserted into the first substrate wafer and the surface of the second substrate wafer opposing said first substrate wafer is entirely covered by a membrane, into which a micro-structurized perforation is provided at least in the section of the passage openings, said micro-structurized perforation being for forming transmission areas.

4. The microcolumn reactor as claimed in claim 3, wherein the membrane is a perforated polymeric foil.

5. The microcolumn reactor according to claim 2, wherein the first and the second substrate wafers are anodically bonded to one another.

6. The microcolumn reactor according to claim 2 or 3, wherein the first and the second substrate wafers are connected to one another by adhesives outside of the channel.

7. The microcolumn reactor according to claim 3, wherein the first and the second substrate wafers are attached to one another by externally provided clamping means.

8. The microcolumn reactor according to claim 1, 2, or 3, wherein said passage openings are connected to a second channel in the second substrate wafer and the second channel extends to a rim of the substrate.

9. The microcolumn reactor, according to one of claims 1–5 and 7, wherein the channel is defined by a plurality of passage openings, and respectively correlated passage openings, which constitute an inlet and an outlet, and passage openings, which define a section of the channel, are arranged relative to one another equidistantly or at different distances.

10. The microcolumn reactor according to claim 9, wherein said plurality of the correlated passage openings are alternatively on a common substrate wafer or fluidically connect a plurality of discrete microcolumn reactors, the respective distances between correlated passage openings, each pair of which together form one inlet and one outlet, being of different length, as determined by requirements of an actual reaction process.

11. The microcolumn reactor according to claim 1, wherein a plurality of substrate wafers, each having a channel and at least two passage openings therein, are fluidically interconnected with one another in a manner selected from: in parallel in a single plane, serially in a plurality of planes, and in a matrix, combining both parallel, single plane and series, multi-plane interconnections, and wherein further components are provided at preselectable connection sites.

12. The microcolumn reactor according to claim 1, wherein a plurality of substrate wafers, each having a channel and at least two passage openings therein, are fluidically interconnected with one another in a manner selected from: in parallel in a single plane, serially in a plurality of planes, and in a matrix, combining both parallel, single plane and series, multi-plane interconnections, and wherein further micro-structurized components are provided and integrated in the entire system.

13. The microcolumn reactor according to claim 2, wherein the passage openings are positioned perpendicular to an exterior surface of said second substrate wafer, and each passage opening having an hourglass shape formed by two frusto-pyramidal sections, each with large and small base surfaces, said two frusto-pyramidal sections abutting one another and inverted upon one another at an intersection of their said small base faces, said second substrate wafer is an Si(100)-wafer having an etching mask on two opposite faces thereof, a first etching mask on one face of said second substrate wafer having transmission areas at least across said passage openings, and a second etching mask on an opposite face of said second substrate mask being provided with recesses having openings which correspond to a smallest inside cross section of said passage openings.

14. The microcolumn reactor according to claim 8, wherein said second substrate wafer is one of a Si-wafer of 100-orientation and 110-orientation, which has a sieve pore membrane mask structure on a side thereof, which, in a vicinity of said second channel further has a window corresponding to a width of said second channel, said window extending up to a rim of said second substrate wafer, and an opposite side of said second substrate wafer is entirely covered by a protective etching resistant coating.

15. The microcolumn reactor according to claim 1, wherein the membrane is a nano-porous, thin-layer membrane, having pore sizes of 5 to 500 nm.

* * * * *